United States Patent [19]

Rohr et al.

[11] 4,368,431

[45] Jan. 11, 1983

[54] ELECTROCHEMICAL MEASURING DEVICE FOR DETERMINING THE OXYGEN CONTENT IN GASES

[75] Inventors: Franz-Josef Rohr, Absteinach; Rudolf Krapf, Leimen, both of Fed. Rep. of Germany

[73] Assignee: Brown, Boveri & Cie Aktiengesellschaft, Mannhein-Käfertal, Fed. Rep. of Germany

[21] Appl. No.: 206,380

[22] Filed: Nov. 13, 1980

[30] Foreign Application Priority Data

Nov. 13, 1979 [DE] Fed. Rep. of Germany ....... 2945698

[51] Int. Cl.³ .......................................... G01N 27/00
[52] U.S. Cl. ................................................ 324/464
[58] Field of Search .............. 324/464, 466, 467, 71 R

[56] References Cited

U.S. PATENT DOCUMENTS 3,223,873 12/1965 Hampton ............................. 324/464
3,445,757 5/1969 Krucoff .............................. 324/464
3,459,039 8/1969 Grey .................................. 324/464

Primary Examiner—Michael J. Tokar
Attorney, Agent, or Firm—Herbert L. Lerner; Laurence A. Greenberg

[57] ABSTRACT

Electrochemical measuring device for determining the oxygen content in gases with approximately constant pressure, especially in combustion exhaust gases, with an oxygen ion-conducting solid electrolyte having two electrodes connected to a voltage source, and measuring changes in current. In combination with the electrical measuring device, a constriction is disposed in the path of the constant pressure gas stream with the constriction having a passageway of cross sectional area to pass the gas stream at the velocity of sound under the condition of critical pressure ratio dependent on a ratio of the pressure at the outflow side of the inflow side of the constriction which brings about sound velocity of the gas stream.

19 Claims, 6 Drawing Figures

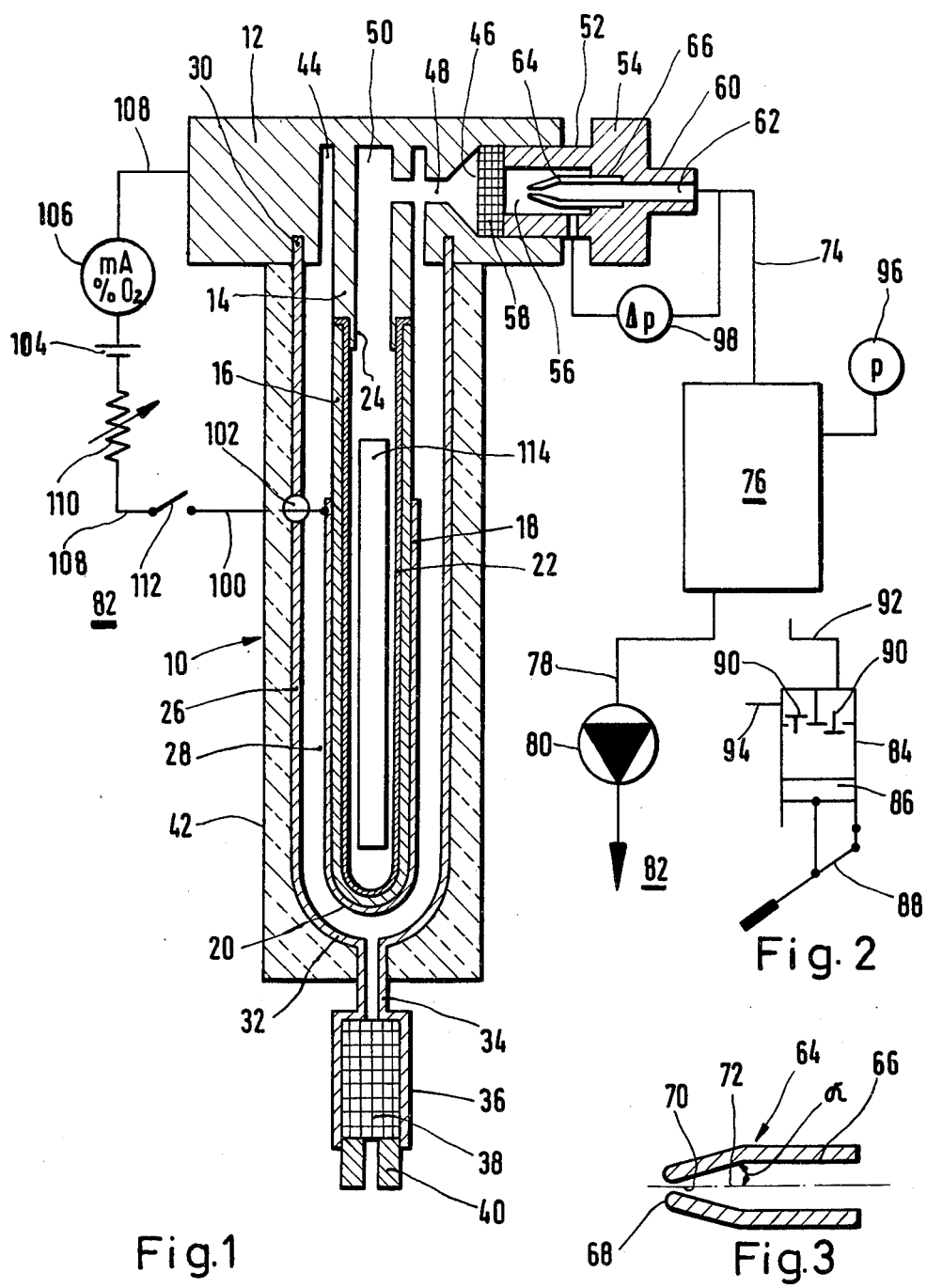

ELECTROCHEMICAL MEASURING DEVICE FOR DETERMINING THE OXYGEN CONTENT IN GASES

BACKGROUND OF THE INVENTION

1. Field of the Invention

The invention relates to an electrochemical measuring device for determining the oxygen content in gases with approximately constant pressure, especially in combustion exhaust gases, with an oxygen ion-conducting solid electrolyte which is provided with at least two electrodes, of which at least a first electrode can be exposed to a sufficient degree to a constant gas stream provided for the measurement and both electrodes can be connected to a voltage source, a current measuring device being inserted into the circuit, and to the use of such measuring device for controlling the fuel-air ratio of a burner for fluid fuels.

2. Description of the Prior Art

In one known measuring device of this type, an electric d-c voltage is applied to the electrodes and the first electrode, acting as a cathode, is exposed to the gas stream to be measured. This extracts the oxygen component of the gas stream electrolytically from the gas stream. This oxygen component is then transported in the form of oxygen ions through the solid electrolyte to the second electrode and is oxidized there to oxygen molecules. The current which then flows and is measured by the current measuring device is a measure for the oxygen ion transport and thus for the oxygen content of the gas stream.

However, in order to be able to give quantitative information regarding the oxygen content, it is necessary to extract all the oxygen from the gas stream, to measure, if necessary, the magnitude of the gas stream, and to hold the gas stream constant during the measurement. While the first requirement can be met by sufficient size of the electrodes and the second requirement in a simple manner by a calibration, the third requirement, namely, holding the gas stream constant, is usually difficult and can be met only with a large expenditure of technical means.

SUMMARY OF THE INVENTION

An object of the invention is to provide an electrochemical measuring device of the type mentioned at the outset in which the gas stream can be held at a constant value in a simple manner and, therefore, without expensive designs. In addition, the measuring device should be largely free of maintenance and operationally highly reliable.

With the foregoing and other objects in view, there is provided in accordance with the invention an electrochemical measuring device for determining oxygen content in gases with approximately constant pressure, especially in combustion exhaust gases, comprising a housing with a gas inlet and a gas outlet for passage of a constant pressure gas stream therethrough, an ion-conducting solid electrolyte with a first and a second electrode disposed in the housing to provide a passageway therein for contact of said constant pressure gas stream with said first electrode for measurement of the oxygen content in the gas, said first and second electrdoes connected by electrical conductors to an electric current source and a current measuring device, the combination therewith of a constriction in the path of the constant pressure gas stream, said constriction having a passageway of cross sectional area to pass the gas stream at the velocity of sound under the condition of critical pressure ratio dependent on a ratio of the pressure at the outflow side of the constriction to the pressure at the inflow side of the constriction which brings about sound velocity of the gas stream.

In accordance with the foregoing, there is provided a method of controlling the fuel-air ratio of a burner for fluid fuels in which fuel to the burner is regulated by a valve and air to the burner is regulated by an air throttle, and combustion products generated by burning the fuel pass through and are discharged from a combustion chamber, comprising bleeding a small stream of discharging combustion gases and passing the gases through an electrochemical measuring device for determining oxygen content in gases with approximately constant pressure, comprising a housing with a gas inlet and a gas outlet for passage of a constant pressure gas stream therethrough, an ion-conducting solid electrolyte with a first and a second electrode disposed in the housing to provide a passageway therein for contact of said constant pressure gas stream with said first electrode for measurement of the oxygen content in the gas, said first and second electrodes connected by electrical conductors to an electric current source, the combination therewith of a constriction in the path of the constant pressure gas stream, said constriction having a passageway of cross sectional area to pass the gas stream at the velocity of sound under the condition of critical pressure ratio dependent on a ratio of the pressure at the outflow side of the constriction to the pressure at the inflow side of the constriction which brings about sound velocity of the gas stream, activating a control unit by an electric current from the electrochemical measuring device in accordance with the measurement therein of the oxygen content of the combustion gases, regulating the air intake to the burner in accordance with the oxygen content of the combustion gases by means of the control unit connected to an air throttle positioning device controlling the setting of the air throttle, and regulating the fuel fed to the burner in accordance with the oxygen content of the combustion gases by means of the control unit connected to a fuel valve positioning unit controlling the setting of the fuel valve.

Other features which are considered as characteristic for the invention are set forth in the appended claims.

Although the invention is illustrated and described herein as embodied in an electrochemical measuring device for determining the oxygen content in gases, it is nevertheless not intended to be limited to the details shown, since various modifications may be made therein without departing from the spirit of the invention and within the scope and range of equivalents of the claims.

BRIEF DESCRIPTION OF THE DRAWINGS

The invention, however, together with additional objects and advantages thereof will be best understood from the following description when read in connection with the accompanying drawings, in which:

FIG. 1 shows a longitudinal section through the electrochemical measuring device of the invention with a constriction in the form of a nozzle;

FIG. 2 is a longitudinal section through a suction pump for manual operation which as an embodiment variant can be connected to the buffer space of FIG. 1;

FIG. 3 shows a longitudinal section through the nozzle according to FIG. 1 as an enlarged detail;

DETAILED DESCRIPTION OF THE INVENTION

Figure 4:
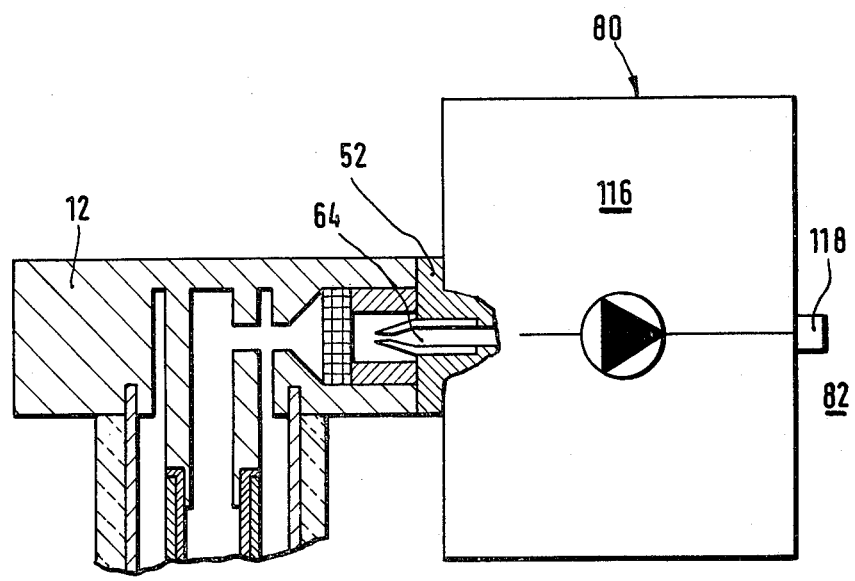
FIG. 4 is an embodiment variant of the subject of FIG. 1, in which the suction device is an electric suction pump fastened directly to the base body of the measuring device.

At least one constriction with a passage cross section passing an adequate gas stream at the sound velocity of the gas is arranged in the path of the gas stream and a pressure ratio which brings about sound velocity of the gas stream in the constriction, can be set between the outflow side and the inflow side of the constriction.

Use is, therefore, made of a law of physics stating that the gas can flow at most with the velocity of sound through a constriction or choke point which connects an inflow space to an outflow space, if a given pressure ratio between the outflow space and the inflow space is not exceeded. The sound velocity depends here on the variables of the state of the gas stream in the constriction. If now the pressure and the temperature of the gas stream in the inflow space are constant, then the gas velocity in the constriction is also constant and completely independent of the counterpressure of the gas stream on the outflow side, if indeed the given pressure ratio is not exceeded. This pressure ratio is known under the name of critical pressure ratio; it depends on the atomic number of atoms in the gases and is 0.528 for two-atom gases, i.e., also for combustion exhaust gases, and can be calculated (see Herning, "Stoffströme in Rohrleitungen", flow matter in pipes, 1957, VDI-Verlag, Düsseldorf).

For the layout of the passage cross section of the constriction, it must be noted that the gas flows with the velocity of sound at the narrowest point of the constriction, where the cross section determining the flow can be smaller than the actually existing passage cross section. This is due to the contraction of the gas stream in the constriction. The actual value for the critical pressure ratio can, furthermore, deviate from the calculated value, which is true particularly if the flow through the constriction is subject to friction losses. By calibrating the measuring device, which may be necessary for the determination of the magnitude of the gas stream, the critical pressure ratio, from which point on the gas stream is constant, can easily be determined.

In principle, the constriction could be of any desired form, for instance in the form of a capillary; it is advantageous, however, if the constriction has the form of an orifice or, in particular, of a nozzle. In addition to easy fabrication, there is the advantage that the friction losses in the constriction are small and therefore, better agreement with the precalculated values for the critical pressure ratio is obtained.

In order to reduce the wear of the passage point and to prevent corrosion, the aperture or nozzle can consist of glass.

In the individual case, the passage cross section, i.e. the cross sectional area of the passage way of the constriction through which the gases pass should be matched to the size of the gas stream. A design which is recommended for a canal adjoining the first electrode with a cross section of about 10 to 20 mm$^2$, may have a passage cross section of about 0.8 mm$^2$ to $20 \times 10^{-4}$ mm$^2$.

It is also advisable to arrange the constriction after the first electrode, as seen in the flow direction, since thereby dirt particles which are carried along by the gas stream in spite of the insertion of filters, can settle in the flow canals preceding the constriction, and the danger of clogging is practically eliminated.

It is basically immaterial how the required pressure ratio between the outflow side and the inflow side is produced. But, if the gas stream has a pressure which is approximately equal to the ambient pressure, for instance, the ambient pressure ±20%, then a suction device which causes the required pressure ratio, preferably a suction pump, can be connected to the outflow side of the constriction. Fluctuations of the suction output have no influence on the constancy of the gas stream as long as the critical pressure ratio is maintained or is smaller.

Advantageously, a buffer space which smoothes out irregularities of the suction device, is inserted between the latter and the outflow side of the constriction. The buffer space preferably has a volume which could take up the gas stream for a period of 15 to 60 minutes.

In conjunction with the buffer space, the suction device may be designed for intermittent operation, especially for hand operation. Thereby, sufficient underpressure is produced in the buffer space which maintains the flow of the gas stream at least for short-time measurements after the suction pump is shut down. In order to measure the pressure in the buffer space and thus, the pressure ratio, it is advantageous to equip the buffer space with a manometer. Optionally, it may also be advisable to connect a difference-pressure manometer to the inflow side and the outflow side for the direct determination of the pressure ratio.

Further advantages and recommended features of the invention will be seen from the following description of embodiment examples in conjunction with the schematic drawings.

Like parts are provided with the same reference symbols in the individual figures. In the individual figures, recurring parts are furthermore provided with reference symbols only to the extent necessary for their understanding.

Referring to FIG. 1, the electrochemical measuring device embraces a measuring cell 10 with an approximately rectangular base body 12, made for instance, of metal. From the one base surface of the base body 12 protrudes a circular-cylinder-shaped projection 14. A solid-electrolyte tube 16 is fastened to the free end of projection 14. The solid-electrolyte tube 16 is provided on its outside with a first electrode 18 which cover, as seen from the closed tip 20, about two-thirds of the length of the solid-electrolyte tube 16. The second electrode 22 is on the inside of the solid-electrolyte tube 16, and extends from the tip 20 to the fastening point of the solid-electrolyte tube 16 at the projection 14 and is in electrically conducting contact with the projection 14. This is achieved by the second electrode 22 being in contact with the centering projection 24.

The electrodes 18 and 22 consist of a ceramic or metallic material, through which the oxygen can pass unimpeded, for instance, by making the material porous. Examples of materials suitable for this purpose are, silver or platinum. As material for the oxygen ion-conducting solid-electrolyte tube, zirconium oxide which is doped with calcium oxide can be used.

The solid-electrolyte tube 16 provided with electrodes is surrounded by a tubular envelope 26, so that a space 28 with an annular cross section is formed between the first electrode 18 and the tubular envelope 26. The width of this space 28 in the radial direction is about 0.3 to 2 mm and preferably, about 0.5 mm. For the sake of clarity, this width is shown larger in the figures. The tubular enclosure 26 is inserted into a ring-shaped recess 30 of the base body 12 and is fastened there, and its other end is closed off in dome-fashion. The distance of the terminating dome 32 from the first electrode 18 of the likewise dome-shaped tip 20 being approximately equal to the distance between the cylindrical part of the tubular enclosure 26 and the first electrode 18.

A tubular stub 34 is provided at the tip of the closing dome 32. Stub 34 has in an expanded section 36, a gas filter 38 which may consist, for instance, of cotton or a porous ceramic body. The expanded section 36 is closed off by a nipple 40 with an axial hole, through which the gas to be measured is fed. The entire tubular enclosure 26 is further surrounded by an insulating jacket 42, which extends up to the base body 12. Mineral wool, for instance, can be used as the material for the insulating jacket.

The ring-shaped projection 14 arranged at the base body 12 is surrounded by a concentric annular gap 44 which extends in the base body and, on the one hand, opens into the space 28 and, on the other hand, is connected to a space 46 of circular cross section which extends transversely to the longitudinal axis of the measuring cell. The connecting hole 48 extending transversely to the longitudinal axis is continued in the direction toward the longitudinal axis, so that the interior 50 of the projection 14, which forms a unit with the interior of the solid electrolyte, is connected to the space 46.

The space 46, which has preferably the shape of a hole, has a thread, into which an insert 52 is screwed by means of a head 54 provided at the insert. The portion of the insert 52 protruding into the base body 12 has the form of an annular ring and clamps a disc-shaped filter 58 between itself and a conical taper of the space 46. The taper then forms the transition of the space 46 to the connecting hole 48. The material of the filter 58 is identical with that of the gas filter 38.

At the head 54, an outward-protruding connecting nipple 60 is arranged centered, through which a central canal 62 leads to the recess 56. In the region of its inner outlet, the canal 62 has a step, in which the nozzle 64 with its cylindrical portion 66 is fastened, the nozzle 64 protruding freely into the recess 56.

The design of the nozzle is best seen from FIG. 3, which shows the nozzle in enlarged detail. Accordingly, the entrance opening 68 of the nozzle is rounded and leads to the narrowest passage cross section 70, which is followed by a conical expansion 72, with the aperture angle $\alpha$ of the expanded section 72 being about 8° to 18° and preferably, 10° to 15°. The expanded section 72 is followed by the cylindrical region 66.

Figure 5:
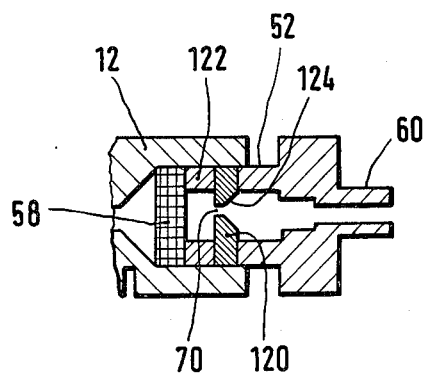
FIG. 5 is a longitudinal section through an embodiment variant of the constriction in the form of an orifice.

The narrowest point of the passage cross section 70 is now chosen so that if a sufficient amount of gas passes through it, the gas flows through it with the velocity of sound. In the present embodiment example, in which the space 28 has a cross section of about 10 to 20 mm$^2$, a value of about $0.8$ to $20 \times 10^{-4}$ mm$^2$ can be considered as a ballpark value for the passage cross section 70. The total length of the nozzle is about 15 to 30 mm and the length of the expanding section 72 is between 5 and 10 mm, with an inside diameter of the cylindrical section 66 of about 5 to 8 mm. Glass serves as the preferred material for the nozzle, and also sapphire pierced by laser beams can be recommended. The gas-carrying cross section of the nozzle is circular; the same applied also to the orifice 120 (FIG. 5).

As can further be seen from FIG. 1, the nozzle connects the recess 56, which forms the inflow side of the gas, to the canal 62 which represents the outflow side of the nozzle.

The connecting nipple 60 is connected, via a connecting line 74, to a buffer space 76 which is connected via a further line 78 to a suction device 80, for instance, in the form of a gas pump. The outlet of suction device 80 leads to the outer space or atmosphere 82 or, especially in the case of poisonous gases, into a collecting space.

In FIG. 2, an embodiment variant with respect to the suction device is shown, which can be connected to the buffer space 76 instead of the suction device 80. According to FIG. 2, the suction device consists of a hand pump 84, the piston 86 of which can be operated by a pump lever 88, so that via the indicated valves 90, gas can be drawn from the buffer space 76 via the line 92 and ejected through the outlet 94 to the outside.

To determine the pressure of the gas stream, a manometer 96 is arranged at the buffer space 76, or optionally, a difference-manometer 98 can be inserted between the recess 56 and the connecting line 74 or the canal 62.

An electric line 100 leads from the first electrode 18 radially to the outside space 82, so that the required measuring voltage can be applied to the electrodes 18 and 22. A bead of insulation 102 is inserted at the point of penetration through the tubular enclosure 26. The second electrode 22 is connected to the base boby 12 in an electrically conducting manner via the centering projection 24 and the projection 14, so that the base body 12, together with the electric line, serve as the electrical terminals of the electrodes. To these terminal is fed via electric lines 108 the voltage required for the measurement from a d-c voltage source 104, for instance, in the form of an electric battery, to a current measuring device 106, for instance, a milliammeter, a variable resistor 110. An electric switch 112 is inserted into the circuit. An electric heating device 114 is arranged in the interior of the solid electrolyte tube 16 to bring the solid-electrolyte tube 16 to the operating temperature. The electric leads going to the heating device 114 are not shown in FIG. 1.

Before oxygen measurements can be performed with the above-described measuring device, an initial adjustment or calibration should be made, which is best carried out immediately when the measuring device is manufactured. For this purpose, it is simplest to use a gas which is similar to the gas to be measured chemically and physically. If the measuring device is to be used for determining the oxygen content in exhaust gases, air can be used for the calibration. The critical pressure ratio for air as a two-atom gas is then 0.528.

For the initial adjustment, the heating device 114 is first put in operation and then, the suction device 80 and its suction output is adjusted so that the pressure ratio between the outflow side 62 and the inflow side 56 of the nozzle 64 is equal to the critical pressure ratio or, preferably, smaller. The adjustment is made by means of the difference pressure manometer 98. If the pressure of the fed-in calibration gas is known, for instance, if ambient air is drawn in, it is also sufficient to measure the pressure on the outflow side of the nozzle, for instance, the pressure in the buffer space 76 for determining the pressure ratio. If the initial adjustment of the suction device 80 has been made once in this manner, further continuous monitoring of the pressure ratio is not necessary if this adjustment is retained. A gas stream of constant size is therefore assured over extended periods of operation.

In case the gas to be measured is fed to the measuring device at overpressure, a suction device 80 and, possibly, a buffer space 76 are not required if the outflow side 62 of the nozzle is at lower pressure, for instance, by being connected to the outside. The desired pressure ratio thus adjusts itself.

If now the initial adjustment has been made in the above-described manner and the solid electrolyte has been brought to the operating temperature, the switch 112 is closed and a d-c voltage of about IV is applied to the electrodes 18, 22. This voltage can be controlled by the variable resistor 110. To the reading of the current measuring decive 106, an oxygen content of 21 volume percent is now assigned. Since with the present measuring principle, the relationship between the oxygen content of the gas to be measured and the current flowing in the measuring circuit is linear, a single measurment point suffices for the calibration.

If the oxygen content of combustion exhaust gases is now to be measured with the measuring device, the latter must be connected by means of the nipple 40 and, if required, with the interposition of a gas cooler, to the exhaust gas line. The suction device 80 then draws a constant gas stream through the measuring device along the following path: Gas filter 38, space 28, connecting hole 48, space 46, filter 58, recess 56 which is equivalent to the inflow side of the nozzle, nozzle 64, canal 62 which is equivalent to the outflow side of the nozzle, buffer space 76 and the suction device 80. When the gas stream flows past the first electrode 18, the oxygen contained in the gas stream is extracted, conducted through the solid electrolyte in the form of ions and is oxidized to oxygen again at the second electrode 22, and given off to the interior of the solid-electrolyte tube. The oxygen is then discharged through the radial connecting hole 48 provided in the projection 14 and is admixed to the gas stream. The current then flowing, with the switch 112 closed, from the d-c voltage source 104 via the electrodes 18, 22 is determined by the current measuring device 106. This current is a measure of the oxygen content of the gas; optionally, the readings of the current measuring device may be directly in volume percent oxygen.

In most cases, the suction device will be an electric suction pump. For short measurements, for instance, for operational supervision, it is advisable to employ a hand pump 84 instead of the suction device 80. Hand pump 84 is shown in FIG. 2. By means of the hand pump 84, which is connected to the buffer space 76, an underpressure sufficient for generating the critical pressure ratio is produced in the buffer space and held constant by the action of the buffer space. If the underpressure in the buffer space 76 required for generating the critical pressure ratio drops too low, intermittent operation of the hand pump 84 is possible because the underpressure of the buffer space 76 assures the constant gas flow required for the measurement between the operating intervals of the pump.

In FIG. 4, an embodiment variant of the subject of the invention with respect to the suction device 80 is shown. While in the measuring device according to FIG. 1, the suction device 80 consists of a separate part, the suction device 80 is fastened directly to the base body 12 in the embodiment example according to FIG. 4. To this end, the suction device 80 is designed as an electric suction pump 116 and is fastened, preferably detachably, directly to the insert 52. The outlet 118 of the suction pump opens directly into the outside space 82. The present embodiment has a more compact design than that of FIG. 1.

In FIG. 5, the region of the insert 52 is shown as a detail and as an embodiment variant. The constriction inserted into the path of the gas stream is designed here as an orifice 120. The latter consists of a circular disc which is clamped between the insert 52 and an intermediate ring 122 braced against the filter 58. The orifice 120 is provided with a preferably central opening which constitutes the passage cross section 70. In order to keep the friction losses in the flow through the passage cross section low, the orifice 120 has on the outflow side a conical taper 124 of the cylindrical passage cross section. The thickness of the orifice is about 2 to 5 mm, and the taper 124 goes through approximately ⅔ of the orifice thickness. Glass is preferably the material for the orifice.

Figure 6:
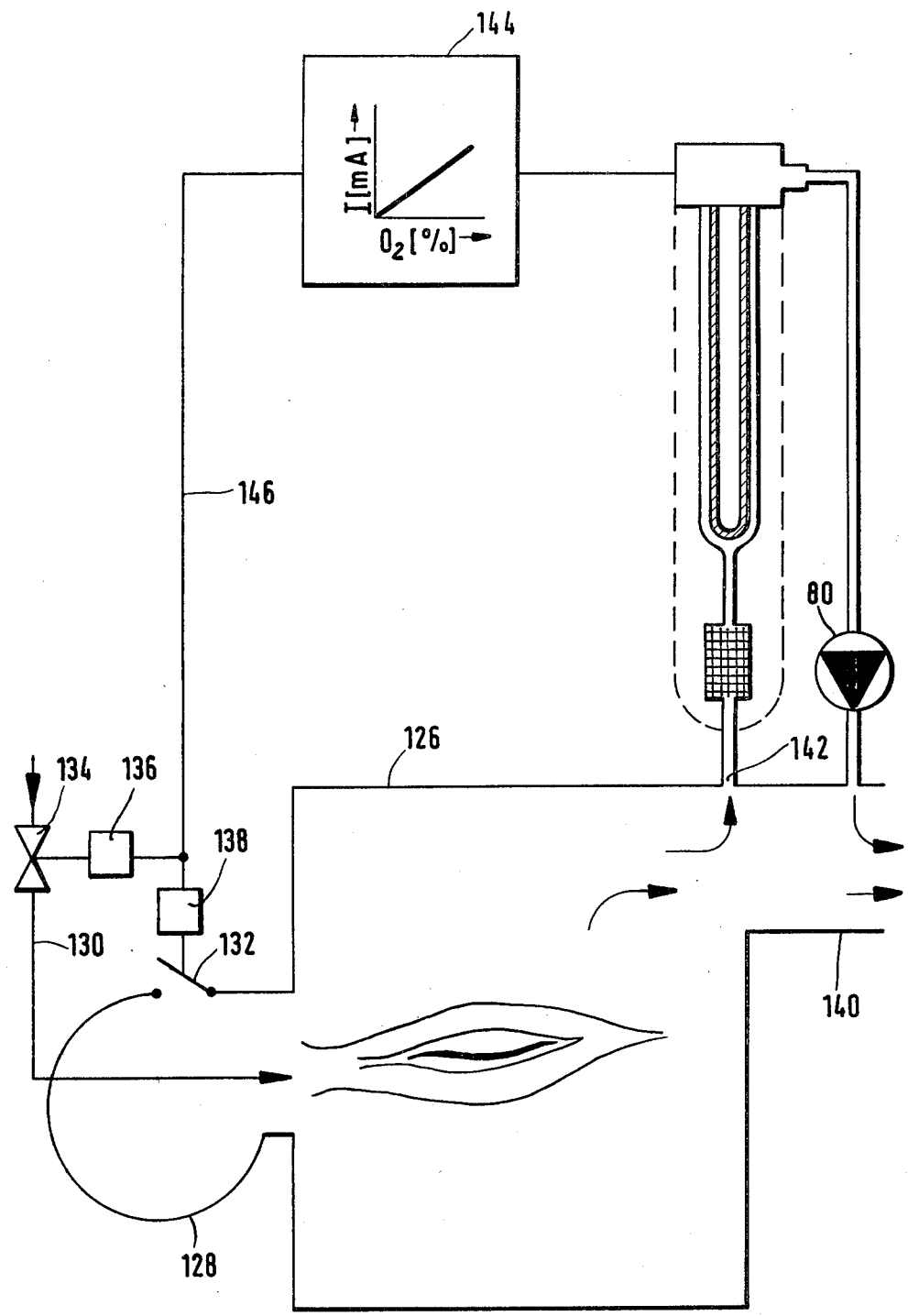
FIG. 6 is the measuring device according to the invention together with a fire box.

In FIG. 6, a preferred application of the measuring device, according to the invention, for the combustion control of burners is shown. A boiler 126 is equipped with a burner 128 for fluid fuels such as gas or oil. The fuel is fed via a pipe 130 and the combustion air via an air throttle 132. In the pipeline 130, a control valve 134 with a positioning device 136 is provided, while the air throttle 132 is provided with a positioning device 138. The measuring device according to the invention is connected to the exhaust gas canal 140, through which the combustion exhaust gases flow to the stack, and the gas stream drawn from the exhaust gas canal through the measuring device is conducted downstream from the take-off point 142 back into the exhaust gas canal 140. In the present embodiment example, the suction device is designed as a continuously operating electric suction pump, so that a buffer space can be dispensed with.

In the present case, a control unit 144 is connected to the measuring device via electric lines instead of or in addition to a current measuring device. In the schematically shown control unit 144, the linear relationship between the oxygen content of the measurement gas and the current delivered by the measuring device in milliamps is indicated. The output of the control unit 144 is in functional connection with the positioning devices 136 and 138, for instance, via electric lines 146.

During the operation of the burner 128, combustion exhaust gases are drawn through the measuring device by the suction device 80 and their oxygen content is determined. Since, for efficient combustion, the combustion exhaust gases should contain as little oxygen as possible, control commands are derived in the control unit 144 from the oxygen signals determined in the measuring device; these commands are fed via the line 146 to the positioning device 138 which acts on the air throttle 132 and/or to that positioning device 136 which acts on the control valve 134. The control unit 144 is now programmed so that the combustion air supply to the burner is regulated in such manner that by changing the air throttle 132 an oxygen content as low as possible is present in the exhaust gases. Optionally, also the fuel supply can be influenced via the positioning device 136, should the influence on the air throttle 132 be insufficient. In this manner, an optimal adjustment of the burner 128 and, thereby, proper, efficient combustion is ensured under any operating conditions.

Instead of an arrangement of the suction device 80 on the outflow side of the nozzle, it is equally feasible to arrange a pressurizing device, for instance, in the form of a pressure pump, in that line which is connected to the nipple 40 and conducts the gas to the measuring device (see FIG. 1).

With respect to the heating device 114, it should further be noted that no constant and also no specific temperature is necessary for the operation of the measuring device. The solid-electrolyte tube 16 must merely be heated to a temperature which is above a temperature limit of about 400° C.

We claim:

1. Electrochemical measuring device for determining oxygen content in gases with approximately constant pressure, especially in combustion exhaust gases, comprising a housing with a gas inlet and a gas outlet for passage of a constant pressure gas stream therethrough, an ion-conducting solid electrolyte with a first and a second electrode disposed in the housing to provide a passageway therein for contact of said constant pressure gas stream with said first electrode for measurement of the oxygen content in the gas, said first and second electrodes connected by electrical conductors to an electric current source and a current measuring device, the combination therewith of a constriction in the path of the constant pressure gas stream, said constriction having a passageway of cross sectional area to pass the gas stream at the velocity of sound under the condition of critical pressure ratio dependent on a ratio of the pressure at the outflow side of the constriction to the pressure at the inflow side of the constriction which brings about sound velocity of the gas stream.

2. Electrochemical measuring device according to claim 1, wherein said constriction is formed with a circular disc havng a central opening.

3. Electrochemical measuring device according to claim 1, wherein said constriction is formed by a nozzle.

4. Electrochemical measuring device according to claim 2, wherein said disc consists of glass.

5. Electrochemical measuring device according to claim 3, wherein said nozzle consists of glass.

6. Electrochemical measuring device according to claim 1, wherein said passageway for contact of said constant pressure gas stream, adjacent to the first electrode, has a cross section of about 10 to 20 mm$^2$, and wherein said passageway of the constriction has a cross section at its narrowest point of about 0.8 to $20 \times 10^{-4}$ mm$^2$.

7. Electrochemical measuring device according to claim 6, wherein said constriction is formed with a circular disc having a central opening.

8. Electrochemical measuring device according to claim 6, wherein said constriction is formed by a nozzle.

9. Electrochemical measuring device according to claim 1, wherein said constriction is disposed in the path of the constant pressure gas after the gas flows past said first electrode.

10. Electrochemical measuring device according to claim 9, wherein said constriction is formed with a circular disc having a central opening.

11. Electrochemical measuring device according to claim 9, wherein said constriction is formed by a nozzle.

12. Electrochemical measuring device according to claim 9, wherein said passageway for contact of said constant pressure gas stream, adjacent to the first electrode, has a cross section of about 10 to 20 mm$^2$, and wherein said passageway of the constriction has a cross section at its narrowest point of about 0.8 to $20 \times 10^{-4}$ mm$^2$.

13. Electrochemical measuring device according to claim 1, wherein a suction device to cause said pressure ratio is connected to the outflow side of the constriction.

14. Electrochemical measuring device according to claim 13, wherein the suction device is a suction pump.

15. Electrochemical measuring device according to claim 13, wherein a buffer space is inserted between the suction device and outflow side.

16. Electrochemical measuring device according to claim 14, wherein the suction pump is designed for intermittent operation.

17. Electrochemical measuring device according to claim 16, wherein said suction pump is a hand pump.

18. A method of controlling the fuel-air ratio of a burner for fluid fuels in which fuel to the burner is regulated by a valve, and air to the burner is regulated by an air throttle, and combustion products generated by burning the fuel pass through and are discharged from a combustion chamber, comprising bleeding a small stream of discharging combustion gases and passing the gases through an electrochemical measuring device for determining oxygen content in gases with approximately constant pressure, comprising a housing with a gas inlet and a gas outlet for passage of a constant pressure gas stream therethrough, an ion-conducting solid electrolyte with a first and a second electrode disposed in the housing to provide a passageway therein for contact of said constant pressure gas stream with said first electrode for measurement of the oxygen content in the gas, said first and second electrodes connected by electrical conductors to an electric current source, the combination therewith of a constriction in the path of the constant pressure gas stream, said constriction having a passageway of cross sectional area to pass the gas stream at the velocity of sound under the condition of critical pressure ratio dependent on a ratio of the pressure at the outflow side of the constriction to the pressure at the inflow side of the constriction which brings about sound velocity of the gas stream, activating a control unit by an electric current from the electrochemical measuring device in accordance with the measurement therein of the oxygen content of the combustion gases, regulating the air intake to the burner in accordance with the oxygen content of the combustion gases by means of the control unit connected to an air throttle positioning device controlling the setting of the air throttle, and regulating the fuel fed to the burner in accordance with the oxygen content of the combustion gases by means of the control unit connected to a fuel valve positioning unit controlling the setting of the fuel valve.

19. Method according to claim 18, wherein a suction device causing the pressure ratio is connected to the outflow side of the constriction and the gases discharged from the suction device returned to the main stream of combustion gases downstream from the point of bleeding of said small stream.

* * * * *